US008548571B2

(12) United States Patent
He et al.

(10) Patent No.: US 8,548,571 B2
(45) Date of Patent: Oct. 1, 2013

(54) DEVICES AND METHODS FOR PREDICTING AND PREVENTING RESTENOSIS

(75) Inventors: Xuanmin He, Sunnyvale, CA (US); John B. Simpson, Woodside, CA (US); Michael H. Rosenthal, San Carlos, CA (US); John F. Black, San Mateo, CA (US)

(73) Assignee: Avinger, Inc., Redwood City, CA (US)

( * ) Notice: Subject to any disclaimer, the term of this patent is extended or adjusted under 35 U.S.C. 154(b) by 119 days.

(21) Appl. No.: 12/963,536

(22) Filed: Dec. 8, 2010

(65) Prior Publication Data

US 2011/0263936 A1    Oct. 27, 2011

Related U.S. Application Data

(60) Provisional application No. 61/267,811, filed on Dec. 8, 2009.

(51) Int. Cl.
*A61B 1/07* (2006.01)
*A61B 6/00* (2006.01)

(52) U.S. Cl.
USPC .......................................... 600/476; 600/425

(58) Field of Classification Search
USPC ........................ 600/407, 425, 476; 356/450
See application file for complete search history.

(56) References Cited

U.S. PATENT DOCUMENTS

| | | | |
|---|---|---|---|
| 4,178,935 A | 12/1979 | Gekhaman et al. | |
| 4,552,554 A | 11/1985 | Gould et al. | |
| 4,621,353 A | 11/1986 | Hazel et al. | |
| 4,639,091 A | 1/1987 | Huignard et al. | |
| 4,654,024 A | 3/1987 | Crittenden et al. | |
| 4,686,982 A | 8/1987 | Nash | |
| 4,771,774 A | 9/1988 | Simpson et al. | |
| 4,926,858 A | 5/1990 | Gifford, III et al. | |
| 5,000,185 A * | 3/1991 | Yock .............................. | 600/459 |

(Continued)

FOREIGN PATENT DOCUMENTS

| | | |
|---|---|---|
| EP | 1859732 A1 | 11/2007 |
| KR | 2007/0047221 | 5/2007 |

(Continued)

OTHER PUBLICATIONS

Sharma et al.; Optical coherence tomography based on an all-fiber autocorrelator using probe-end reflection as reference; CWJ13; San Francisco, California; CLEO 2004.

(Continued)

*Primary Examiner* — Jacqueline Cheng
(74) *Attorney, Agent, or Firm* — Shay Glenn LLP

(57) ABSTRACT

The present invention relates to methods and devices for predicting restenosis, and for treating atherosclerosis to prevent or reduce the incidence of restenosis. Methods of predicting restenosis in a stenosed peripheral artery may include quantitative histology of the vessel. For example, a method of treating a stenosed artery (and particularly a peripheral artery) may include the steps of determining a level of hypercellularity and one or more of the lipid-richness and extent of inflammatory cell inclusion in the tissue. An index of restenosis based on the hypercellularity and lipid richness and/or extent of inflammatory cell inclusion in the tissue may be determined. Systems for treating or preventing restenosis may include one or more imaging modalities for imaging tissue regions and determining the level of hypercellularity and one or more of the degree of lipid-richness and the extent of inflammatory cell inclusion in the tissue region.

29 Claims, 12 Drawing Sheets

(56) References Cited

U.S. PATENT DOCUMENTS

| | | | |
|---|---|---|---|
| 5,047,040 A | 9/1991 | Simpson et al. | |
| 5,085,662 A | 2/1992 | Willard | |
| 5,182,291 A | 1/1993 | Gubin et al. | |
| 5,190,050 A | 3/1993 | Nitzsche | |
| 5,312,415 A | 5/1994 | Palermo | |
| 5,312,425 A | 5/1994 | Evans et al. | |
| 5,321,501 A | 6/1994 | Swanson et al. | |
| 5,333,142 A | 7/1994 | Scheps | |
| 5,358,472 A | 10/1994 | Vance et al. | |
| 5,383,467 A | 1/1995 | Auer et al. | |
| 5,431,673 A | 7/1995 | Summers et al. | |
| 5,459,570 A | 10/1995 | Swanson et al. | |
| 5,465,147 A | 11/1995 | Swanson | |
| 5,556,405 A | 9/1996 | Lary | |
| 5,632,754 A | 5/1997 | Farley et al. | |
| 5,632,755 A | 5/1997 | Nordgren et al. | |
| 5,674,232 A | 10/1997 | Halliburton | |
| 5,681,336 A | 10/1997 | Clement et al. | |
| 5,690,634 A | 11/1997 | Muller et al. | |
| 5,722,403 A | 3/1998 | McGee et al. | |
| 5,795,295 A | 8/1998 | Hellmuth et al. | |
| 5,830,145 A | 11/1998 | Tenhoff | |
| 5,843,050 A | 12/1998 | Jones et al. | |
| 5,868,778 A | 2/1999 | Gershony et al. | |
| 5,872,879 A | 2/1999 | Hamm | |
| 5,904,651 A | 5/1999 | Swanson et al. | |
| 5,907,425 A | 5/1999 | Dickensheets et al. | |
| 5,935,075 A * | 8/1999 | Casscells et al. | 600/474 |
| 5,938,602 A | 8/1999 | Lloyd | |
| 5,951,482 A | 9/1999 | Winston et al. | |
| 5,951,581 A | 9/1999 | Saadat et al. | |
| 5,951,583 A | 9/1999 | Jensen et al. | |
| 5,956,355 A | 9/1999 | Swanson et al. | |
| 5,957,952 A | 9/1999 | Gershony et al. | |
| 6,001,112 A | 12/1999 | Taylor | |
| 6,007,530 A | 12/1999 | Dornhofer et al. | |
| 6,010,449 A | 1/2000 | Selmon et al. | |
| 6,013,072 A | 1/2000 | Winston et al. | |
| 6,017,359 A | 1/2000 | Gershony et al. | |
| 6,027,514 A | 2/2000 | Stine et al. | |
| 6,048,349 A | 4/2000 | Winston et al. | |
| 6,080,170 A | 6/2000 | Nash et al. | |
| 6,106,515 A | 8/2000 | Winston et al. | |
| 6,110,164 A | 8/2000 | Vidlund | |
| 6,120,515 A | 9/2000 | Rogers et al. | |
| 6,120,516 A | 9/2000 | Selmon et al. | |
| 6,134,002 A | 10/2000 | Stimson et al. | |
| 6,134,003 A | 10/2000 | Tearney et al. | |
| 6,152,938 A | 11/2000 | Curry | |
| 6,152,951 A | 11/2000 | Hashimoto et al. | |
| 6,160,826 A | 12/2000 | Swanson et al. | |
| 6,175,669 B1 | 1/2001 | Colston et al. | |
| 6,193,676 B1 | 2/2001 | Winston et al. | |
| 6,206,898 B1 | 3/2001 | Honeycutt et al. | |
| 6,228,076 B1 | 5/2001 | Winston et al. | |
| 6,241,744 B1 | 6/2001 | Imran et al. | |
| 6,283,957 B1 | 9/2001 | Hashimoto et al. | |
| 6,290,668 B1 | 9/2001 | Gregory et al. | |
| 6,294,775 B1 | 9/2001 | Seibel et al. | |
| 6,299,622 B1 | 10/2001 | Snow et al. | |
| 6,307,985 B1 | 10/2001 | Murakami et al. | |
| 6,445,939 B1 | 9/2002 | Swanson et al. | |
| 6,445,944 B1 | 9/2002 | Ostrovsky | |
| 6,447,525 B2 | 9/2002 | Follmer et al. | |
| 6,451,036 B1 | 9/2002 | Heitzmann et al. | |
| 6,454,779 B1 | 9/2002 | Taylor | |
| 6,482,217 B1 | 11/2002 | Pintor et al. | |
| 6,485,413 B1 | 11/2002 | Boppart et al. | |
| 6,497,649 B2 | 12/2002 | Parker et al. | |
| 6,501,551 B1 | 12/2002 | Tearney et al. | |
| 6,503,261 B1 | 1/2003 | Bruneau et al. | |
| 6,517,528 B1 | 2/2003 | Pantages et al. | |
| 6,542,665 B2 | 4/2003 | Reed et al. | |
| 6,551,302 B1 | 4/2003 | Rosinko et al. | |
| 6,563,105 B2 | 5/2003 | Seibel et al. | |
| 6,564,087 B1 | 5/2003 | Pitris et al. | |
| 6,565,588 B1 | 5/2003 | Clement et al. | |
| 6,579,298 B1 | 6/2003 | Bruneau et al. | |
| 6,615,071 B1 * | 9/2003 | Casscells et al. | 600/474 |
| 6,623,496 B2 | 9/2003 | Snow et al. | |
| 6,638,233 B2 | 10/2003 | Corvi et al. | |
| 6,666,874 B2 | 12/2003 | Heitzmann et al. | |
| 6,687,010 B1 | 2/2004 | Horii | |
| 6,728,571 B1 | 4/2004 | Barbato | |
| D489,973 S | 5/2004 | Root et al. | |
| 6,730,063 B2 | 5/2004 | Delaney et al. | |
| 6,760,112 B2 | 7/2004 | Reed et al. | |
| 6,800,085 B2 | 10/2004 | Selmon et al. | |
| 6,818,001 B2 | 11/2004 | Wulfman et al. | |
| 6,824,550 B1 | 11/2004 | Noriega et al. | |
| 6,830,577 B2 | 12/2004 | Nash et al. | |
| 6,845,190 B1 | 1/2005 | Smithwick et al. | |
| 6,852,109 B2 | 2/2005 | Winston et al. | |
| 6,853,457 B2 | 2/2005 | Bjarklev et al. | |
| 6,856,712 B2 | 2/2005 | Fauver et al. | |
| 6,867,753 B2 | 3/2005 | Chinthammit et al. | |
| 6,879,851 B2 | 4/2005 | McNamara et al. | |
| 6,947,787 B2 | 9/2005 | Webler | |
| 6,961,123 B1 | 11/2005 | Wang et al. | |
| 6,970,732 B2 | 11/2005 | Winston et al. | |
| 6,975,898 B2 | 12/2005 | Seibel | |
| 7,068,878 B2 | 6/2006 | Crossman-Bosworth et al. | |
| 7,074,231 B2 | 7/2006 | Jang | |
| 7,126,693 B2 | 10/2006 | Everett et al. | |
| 7,172,610 B2 | 2/2007 | Heitzmann et al. | |
| 7,242,480 B2 | 7/2007 | Alphonse | |
| 7,261,687 B2 | 8/2007 | Yang | |
| 7,288,087 B2 | 10/2007 | Winston et al. | |
| 7,291,146 B2 | 11/2007 | Steinke et al. | |
| 7,297,131 B2 | 11/2007 | Nita | |
| 7,311,723 B2 | 12/2007 | Seibel et al. | |
| 7,344,546 B2 | 3/2008 | Wulfman et al. | |
| 7,366,376 B2 | 4/2008 | Shishkov et al. | |
| 7,382,949 B2 | 6/2008 | Bouma et al. | |
| 7,426,036 B2 | 9/2008 | Feldchtein et al. | |
| 7,428,001 B2 | 9/2008 | Schowengerdt et al. | |
| 7,428,053 B2 | 9/2008 | Feldchtein et al. | |
| 7,455,649 B2 | 11/2008 | Root et al. | |
| 7,474,407 B2 | 1/2009 | Gutin | |
| 7,485,127 B2 | 2/2009 | Nistal | |
| 7,488,340 B2 | 2/2009 | Kauphusman et al. | |
| 7,530,948 B2 | 5/2009 | Seibel et al. | |
| 7,530,976 B2 | 5/2009 | MacMahon et al. | |
| 7,538,859 B2 | 5/2009 | Tearney et al. | |
| 7,538,886 B2 | 5/2009 | Feldchtein | |
| 7,539,362 B2 | 5/2009 | Teramura | |
| 7,542,145 B2 | 6/2009 | Toida et al. | |
| 7,544,162 B2 | 6/2009 | Ohkubo | |
| 7,545,504 B2 | 6/2009 | Buckland et al. | |
| 7,555,333 B2 | 6/2009 | Wang et al. | |
| 7,577,471 B2 | 8/2009 | Camus et al. | |
| 7,583,872 B2 | 9/2009 | Seibel et al. | |
| 7,616,986 B2 | 11/2009 | Seibel et al. | |
| 7,674,253 B2 | 3/2010 | Fisher et al. | |
| 7,706,863 B2 | 4/2010 | Imanishi et al. | |
| 7,728,985 B2 | 6/2010 | Feldchtein et al. | |
| 7,734,332 B2 | 6/2010 | Sher | |
| 7,738,945 B2 | 6/2010 | Fauver et al. | |
| 7,753,852 B2 | 7/2010 | Maschke | |
| 7,785,286 B2 | 8/2010 | Magnin et al. | |
| 7,813,609 B2 | 10/2010 | Petersen et al. | |
| 7,821,643 B2 | 10/2010 | Amazeen et al. | |
| 7,824,089 B2 | 11/2010 | Charles | |
| 7,944,568 B2 | 5/2011 | Teramura et al. | |
| 7,952,718 B2 | 5/2011 | Li et al. | |
| 8,059,274 B2 | 11/2011 | Splinter | |
| 2001/0020126 A1 | 9/2001 | Swanson et al. | |
| 2002/0019644 A1 | 2/2002 | Hastings et al. | |
| 2002/0082626 A1 | 6/2002 | Donohoe et al. | |
| 2002/0111548 A1 | 8/2002 | Swanson et al. | |
| 2002/0115931 A1 * | 8/2002 | Strauss et al. | 600/420 |
| 2003/0028100 A1 * | 2/2003 | Tearney et al. | 600/431 |
| 2003/0032880 A1 * | 2/2003 | Moore | 600/437 |
| 2003/0045835 A1 | 3/2003 | Anderson et al. | |

| | | |
|---|---|---|
| 2003/0095248 A1 | 5/2003 | Frot |
| 2003/0097044 A1 | 5/2003 | Rovegno |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2004/0082850 A1 | 4/2004 | Bonner et al. |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0141843 A1 | 6/2005 | Warden et al. |
| 2005/0154407 A1 | 7/2005 | Simpson |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0196926 A1 | 8/2007 | Soito et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0147000 A1 | 6/2008 | Seibel et al. |
| 2008/0154293 A1 | 6/2008 | Taylor et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0093764 A1 | 4/2009 | Pfeffer et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0270888 A1 | 10/2009 | Patel et al. |
| 2009/0284749 A1 | 11/2009 | Johnson et al. |
| 2009/0316116 A1 | 12/2009 | Melville et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0274270 A1 | 10/2010 | Patel et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0040238 A1 | 2/2011 | Wulfman et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2012/0041307 A1 | 2/2012 | Patel et al. |
| 2012/0046679 A1 | 2/2012 | Patel et al. |
| 2012/0238869 A1 | 9/2012 | Schmitt et al. |
| 2013/0096589 A1 | 4/2013 | Spencer et al. |

FOREIGN PATENT DOCUMENTS

| | | |
|---|---|---|
| RU | 2185859 C2 | 7/2002 |
| RU | 2218191 C2 | 12/2003 |
| WO | WO 99/23958 A1 | 5/1999 |
| WO | WO 00/54659 A1 | 9/2000 |
| WO | WO 2006/133030 A2 | 12/2006 |
| WO | WO 2008/087613 A2 | 7/2008 |
| WO | WO2009/006335 A1 | 1/2009 |
| WO | WO2009/024344 A1 | 2/2009 |
| WO | WO 2009/094341 A2 | 7/2009 |
| WO | WO 2009/140617 A2 | 11/2009 |

OTHER PUBLICATIONS

Aziz et al.; Chronic total occlusions—a stiff challenge requiring a major breakthrough: is there light at the end of the tunnel?; Heart; vol. 91; suppl. III; pp. 42-48; Jun. 2005.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Wang et al.; Common-path endoscopic Fourier domain OCT with a reference Michelson interferometer; Proceedings of the SPIE; vol. 7566; pp. 75660L-75660L-7; Jan. 2010.

Simpson et. al; U.S. Appl. No. 13/433,049 entitled "Occlusion-Crossing Devices, Imaging, And Atherectomy Devices," filed Mar. 28, 2012.

Emkey et al.; Analysis and evaluation of graded-index fiber-lenses; Journal of Lightwave Technology; vol. LT-5; No. 9; pp. 1156-1164; Sep. 1987.

Linares et al.; Arbitrary single-mode coupling by tapered and nontapered grin fiber lenses; Applied Optics; vol. 29; No. 28; pp. 4003-4007; Oct. 1, 1990.

Suparno et al.; Light scattering with single-mode fiber collimators; Applied Optics; vol. 33; No. 30; pp. 7200-7205; Oct. 20, 1994.

Spencer et al.; U.S. Appl. No. 13/675,867 entitled "Occlusion-Crossing Devices, Atherectomy Devices, And Imaging," filed Nov. 13, 2012.

Patel et al.; U.S. Appl. No. 13/752,325 entitled "Catheter system and method for boring through blocked vascular passages," filed Jan. 28, 2013.

* cited by examiner

DEVICES AND METHODS FOR PREDICTING AND PREVENTING RESTENOSIS

CROSS REFERENCE TO RELATED APPLICATIONS

This patent application claims priority to U.S. Provisional patent application Ser. No. 61/267,811, filed on Dec. 8, 2009, titled "DEVICES AND METHODS FOR PREDICTING AND PREVENTING RESTENOSIS", which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Atherosclerosis is an artery disease believed to arise from endothelial malfunction, accumulation of lipid materials in the intima of artery, inflammatory cell infiltration and reaction, artery wall structure damage, smooth muscle cell proliferation and fibrosis change. These factors may result in artery stenosis and ischemia of supplied organs and severe clinical consequences, such as heart attack in coronary artery stenosis, claudication and critical limb ischemia in occlusive peripheral vascular disease.

Atherosclerosis may be treated by atherectomy (e.g., removal of stenosed tissue). For example, directional atherectomy may use a catheter-based system to excise and retrieve plaque tissue for the transluminal treatment of coronary and peripheral atherosclerotic artery disease. The excision and collection of plaque tissue in directional atherectomy not only leaves behind a large and smooth lumen at the treated artery segment, but may also provide plaque tissue for histopathological analysis and new insights into the mechanism of atherosclerotic progress and variable therapy response.

Atherosclerotic stenoses in coronary and peripheral arteries vary widely in presentation and severity. In peripheral arteries the disease is under-diagnosed and under-treated, amputation rate in the US is staggering at 200,000 per year and recurrence rates following peripheral interventions (atherectomy, angioplasty and stenting) are still high. Peripheral stent fracture and failure of drug eluding stents in the periphery remains a big problem. The Baim-Kuntz coronary model of "bigger is better" has been difficult to apply to peripheral vessels because of the diffuse nature of the disease and the large atherosclerotic burden. A high capacity atherectomy system with on-board real-time imaging to guide plaque resection could potentially overcome the disadvantages in current devices and allow the Baim-Kuntz model to be applied to the peripheral vascular space for the first time.

As mentioned above it is well recognized that peripheral plaque burden is large in comparison to coronary lesions. Current atherectomy systems leave up to 60% of the atheroma atheroma in the vessel as confirmed by intra-vascular intrasound (IVUS). A new image guided atherectomy (IGA) system with greater capacity for tissue management may be better able to safely achieve maximal luminal gain with minimal barotraumas. To achieve this improved acute outcome, a new cutter design combined with imaging near the cutter edge may be used. The method and devices described herein may help guide treatment with such a device, or even in devices that do not include cutting components and/or on-board imaging.

Despite high procedure success rates, excellent patency rate, and low complications, post-intervention restenosis often limits plaque excision methods from becoming a more routine and effective resvasculization procedure for the treatment of coronary and peripheral atherosclerotic artery disease. Thus, there is a need to understand the mechanism of restenosis, and to determine new approaches for preventing and treating post-intervention restenosis.

Although there have been other attempts to histopathologically analyze excised atherosclerotic plaque tissue, the results have generally proven unsatisfactory. For example, the relationship between plaque histopathological components and subsequent restenosis atherosclerotic lesions treated with directional atherectomy device has been controversial. Such plaque histopathological studies and evaluations have been mostly based only on the qualitative presence or absence of different plaque components. Quantitative histological analysis may provide more detail information to help understand the mechanism of restenosis. Herein we describe a method of describing and quantifying various atherosclerotic plaque elements, and devices for applying this analysis. Furthermore, we herein identify specific factors and parameters that correlate with angiographic restenosis rates in coronary atherosclerotic patients treated by directional atherectomy.

We have discovered that histopathological analysis of atherosclerotic artery tissue from patients with cardiovascular disease may be used to predict incidence of restenosis in the artery. More particularly, restenosis of may be predicted based on the histopathological analysis of atherosclerotic tissue (including excised fragments from atherectomy procedures) in patients with atherosclerotic artery disease. The histopathological analysis applied may be quantitative; furthermore, quantitative estimates and ranges are provided which may correlate to restenosis. Applications of the quantitative histological parameters and ranges of values of these parameters are also described.

SUMMARY OF THE INVENTION

The present invention relates to methods and devices for predicting restenosis, and for treating atherosclerosis to prevent or reduce the incidence of restenosis.

In particular, described herein are methods of predicting restenosis in a stenosed peripheral artery based on the quantitative histology of the vessel. For example, a method of treating a stenosed artery (and particularly a peripheral artery) may include the steps of determining a level of hypercellularity, and providing a predictive index of restenosis based on the level of hypercellularity and/or the level of lipid-rich tissue, and/or the level of inflammatory cells in the tissue. Each of these factors may be examined individually, or they may be combined.

These factors (e.g., hypercellularity, lipid-rich regions, inflammatory cells) may be provided as a quantitative and/or qualitative index. For example, hypercellularity may be provided as a percentage of total tissue or a percentage of hypercellularity, or the level of hypercellularity may be used to provide an indicator of "low/medium/high" or the like. An index indicating the likelihood of restenosis (either quantitatively or qualitatively) may be provided by combining one or more of these factors. These factors may also be combined with other factors, such as post-interventional minimal lumen diameter (MLD) to provide a more robust indicator of Also described herein are systems and devices for treating or assisting in the treatment of stenosis by providing an indication of the hypercellularity, lipid-rich regions and/or inflammatory cells in an artery, and particularly a peripheral artery. Systems including visualization methods such as catheter-based imaging systems using Optical Coherence Tomography (OCT) are of particular interest. Systems may also be configured for predicting or indicating if restenosis is to occur. Systems or devices may be configured to show hypercellularity and/or lipid-rich tissue and/or inflammatory cells in an arterial tissue. The systems may be configured to present quantitative or qualitative estimates in real-time.

In some variations devices for treating atherosclerosis may be configured for eat-time or near real-time aging of tissue so that the artery may be treated while imaging the tissue. In general, these devices may be used with one more catheters for imaging and treating the tissue.

For example, described herein are devices for treating atherosclerosis and prevent restenosis. In some variations the devices include: an imaging catheter having a sensor configured to image a portion of an artery; a processor configured to receive images of the artery from the sensor processor and to detect regions of hypercellularity in the artery based on the received images, and further configured to detect regions of either or both: lipid-rich tissue and inflammatory cells in the artery from the received ages; and a display configured to display a modified view of the artery indicating hypercellularity and one or both of lipid-rich tissue and inflammatory cells in the artery.

The device imaging catheter, may be any appropriate catheter, including an atherectomy catheter. Steerable catheters, and catheters having more than one imaging modality may be included (or catheters having one imaging modality). For example, the imaging catheter may be an OCT imaging catheter and the sensor comprises an OCT imaging sensor.

The device (or systems) may include any appropriate processor or processors for taking and analyzing images of the arterial tissue or regions of the artery. A processor may be a dedicated or general purpose processor. The processor may be configured in part as a controller for controlling operation of the various components of the system. In some variations a separate controller may be used. The controller may control operation of the analysis and/or the display of images and the resulting identified tissue regions (e.g., showing regions at high risk for restenosis on a display). As mentioned, in some variations, the processor and display are configured to operate in real or near-real time.

The processor (or processors) may include logic for analyzing and/or controlling the system. For example a device or system may include detection logic configured to detect regions of hypercellularity and either or both: lipid-rich tissue and inflammatory cells in the artery from the received images. The detection logic may be further configured to estimate, measure or count a degree of hypercellularity and one or both of lipid-richness and/or the amount of inflammatory cells (e.g., macrophages, lymphocytes, etc.) in the tissue region. The device or system may also include index logic for calculating an index that combined (and/or weights) the measures, counts, or estimates of hypercellularity and one or both of lipid-richness and/or the amount of inflammatory cells (e.g., macrophages, lymphocytes, etc.) in the tissue region. In some variation the index logic may be included with the detection logic, or vice-versa.

The display may be a visual display, such as monitor, screen, projection, or the like. The display may be configured to highlight one or more regions of overlap indicating both hypercellularity and either or both: lipid-rich tissue and inflammatory cells in the artery on the modified view of the artery. In some variations the display may overlay an image of the artery or a region of the artery with an indication of the likelihood of restenosis, and my include markers indicating the relative location of the catheter or another device such as an atherectomy catheter or the cutting region of an atherectomy catheter. The indicator of the likelihood of restenosis may be a color (e.g., color intensity or color-coding) or numeric (0 to 100, 0 to 10, 0.00 to 1.00, etc.) or percentage indicator.

As mentioned, the processor further may also include index logic configured to determine an index of restenosis based on the degree of hypercellularity and either or both: the degree of lipid-rich tissue and the degree of inflammatory cells in the artery from a region of the artery in the received images. In some variations, the index logic determines the index of restenosis based on the degree of hypercellularity, the degree of lipid-rich tissue and the degree of inflammatory cells from the region of the artery. In variations in which an index of restenosis is determined, the system may display the index of restenosis for the region. For example, the device display may be configured to overlay an indicator of the index of restenosis for the region over a view including the region of the artery.

Also described herein are systems for indicating an enhanced risk of restenosis in an arterial tissue. For example, a system may include: an imaging modality configured to image a region of arterial tissue; and a processor configured to receive the image of the region of arterial tissue from the imaging modality and to determine a measure of hypercellularity and further configured to determine one or both of: a measure of how lipid-rich the tissue region is and a measure of how many inflammatory cells there are associated with the tissue region; and index logic configured to determine an index of restenosis for the tissue region based on the measure of hypercellularity and one or both of the measures of how lipid-rich the first tissue region is and the measure of how many inflammatory cells are associated with the first tissue region. The system may also include an output configured to output the index of restenosis.

As mentioned above, in some variations of the system, the index logic is configured to determine an index of restenosis based on the measure of hypercellularity, the measure of how lipid-rich the first tissue region is, and the measure of how many inflammatory cells are associated with the first tissue region.

Methods of treating atherosclerosis based on an estimate of the risk of restenosis as described herein are also provided. Also taught are methods, devices and systems for determining an enhanced risk of restenosis in an arterial tissue, as well as methods, devices and systems for treating and/or preventing restenosis in an arterial tissue.

For example, described herein are methods of determining an enhanced risk of restenosis in an arterial tissue. In some variations, these methods include the steps of: determining a measure of hypercellularity in a first arterial tissue region; determining one or both of: a measure of how lipid-rich the first tissue region is and a measure of how many inflammatory cells there are associated with the first tissue region; determining an index of restenosis for the first tissue region based on the measure of hypercellularity and one or both of the measures of how lipid-rich the first tissue region is and the measure of how many inflammatory cells are associated with the first tissue region; and presenting the index of restenosis for the first tissue region.

The step of determining an index of restenosis may include determining the index of restenosis for the first tissue region based on the measure of hypercellularity and the measure of how lipid-rich the first tissue region is and the measure of how many inflammatory cells are associated with the first tissue region.

The step of presenting may include displaying an image of the first tissue region with a visual indicator of the index of restenosis. In some variations, the method further includes imaging the first tissue region with an imaging modality configured to detect hypercellularity and/or imaging the first tissue region with an imaging modality configured to detect lipid-rich regions. In any of the devices, system and methods described herein, a measure of hypercellularity may be determined using an imaging modality such as optical coherence tomography to image the arterial tissue or a region (e.g., the "first region") of the tissue.

The step of determining a measure of hypercellularity may include counting or estimating the amount of satellite-to-spindle-shaped smooth muscle cells within stroma. In general, determining a measure, estimate or count of hypercellularity may include determining the density of cells (e.g., muscle cells) within the stroma or a region of stroma fibrotic stroma rich in proteoglycan materials). The step of determining a measure of how lipid-rich a tissue region is may comprise estimating the amount or degree of amorphous material containing cholesterol crystals, loosely aggregated necrotic debris and foam cells. The step of determining a measure of how many inflammatory cells are associated with the first tissue region may include counting or estimating clusters of macrophages and lymphocytes.

In any of the devices, systems and methods described herein, the arterial tissue may be treated with a marker, dye, or indicator, which may help in determining a measure/estimate/count of the degree of hypercellularity, lipid-richness and/or presence of inflammatory cells.

In some variations, the methods described herein may also include the step of inserting a stent adjacent to the first arterial tissue region when the index of restenosis indicates a greater likelihood of restenosis. Other treatment methods may be used as well. For example, tissue (additional tissue in some cases) may be excited, the arterial region treated locally with one or more drugs or therapies (e.g., ablated, heat-treated, etc.), or the like.

In some variations of the methods described herein, tissue (e.g., an arterial tissue region) may be removed from the patient before or during the procedure, including before or during the estimation of hypercellularity, lipid-richness or the presence of inflammatory cells. In some variations it is the removed tissue that is examined; in other variations in is the tissue left behind that is examined; while in still other variations both tissues are examined.

Also described herein are methods of preventing restenosis in an arterial tissue. For example, a method of preventing restenosis may include: determining an index of restenosis for a first arterial tissue region based on a measure of hypercellularity of the first arterial tissue region and one or both of a measure of how lipid-rich the first arterial tissue region is and a measure of how many inflammatory cells are associated with the first arterial tissue region; and inserting a stent adjacent to the first arterial tissue region when the index of restenosis indicates a greater likelihood of restenosis. As mentioned above, in some variations other methods of treating the artery may be used in addition to, or in place of, the insertion of a stent.

The method may further include removing of tissue from the first arterial tissue region, either before (to analyze) or after (to treat). In some variations, the step of determining an index comprises imaging the first arterial tissue region in real or near-real time.

DETAILED DESCRIPTION OF THE INVENTION

Section I, below, describes the key observation that quantitative histology may be used to predict rates of restenosis in patients undergoing atherectomy. In particular, certain levels of hypercellularity may indicate restenosis. The degree of lipid-rich tissue, as well as the level of inflammatory cells in the tissue may also be combined (individually or together) with the level of hypercellularity or other factor to provide an indication (which may be provided as an index) of the likelihood of restenosis. Section II describes how these observations may be applied.

Section I: Quantitative Histology

In an initial study, patients with angiographic follow up data and with a good quality tissue sections for histological evaluation were used. A total 409 specimens from native, primary (de novo) coronary artery lesions, and 354 specimens from restenosis lesion with prior intervention (balloon angioplasty, directional atherectomy or both) were included for the analysis.

Tissue Collection, Process and Slide Scan

Atherosclerotic tissue fragments were removed from the collection chamber of atherectomy catheter and fixed in 10% buffered formalin, processed through graded alcohols, and xylerte, and embedded in paraffin. Tissue sections of 4-6 um thick were cut and stained with hematoxylin and eosin, Masson's trichrome, and elastic van Gieson stains. The stained slides were scanned into digital images using a slide scanner, e.g., ScanScope CS (Aperio, Vista, Calif. 92081).

Characterization of Atherectomy Tissue Specimens

Figure 1:
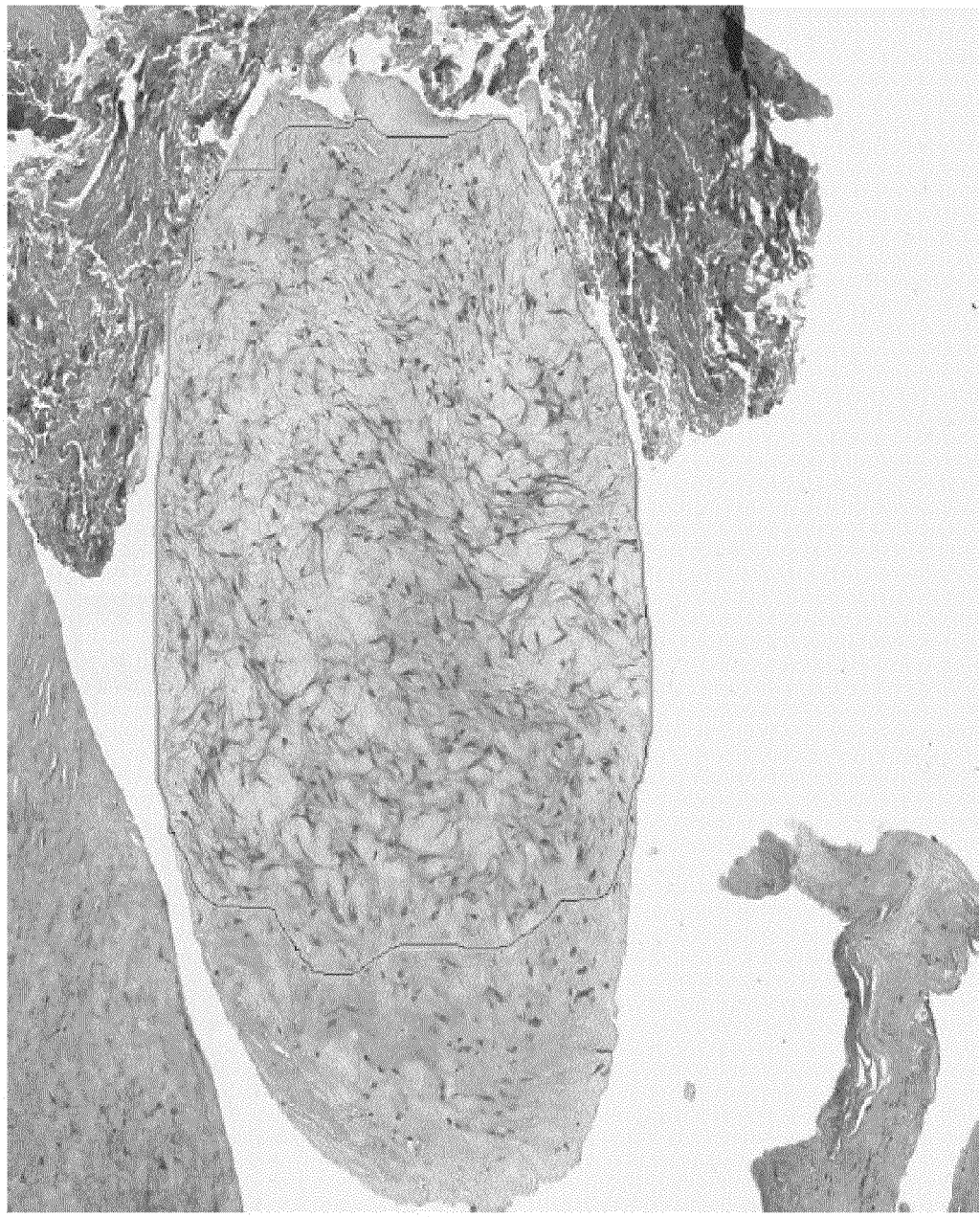
FIG. 1 illustrates hypercellular tissue.

Various histological elements or components were described as follow:

Hypercellular: Hypercellular plaque tissue was characterized by the presence of numerous satellite-to-spindle shaped smooth muscles cells within loose-to-mildly fibrotic stroma rich in proteoglycan materials (see, e.g., FIG. 1).

Figure 2:
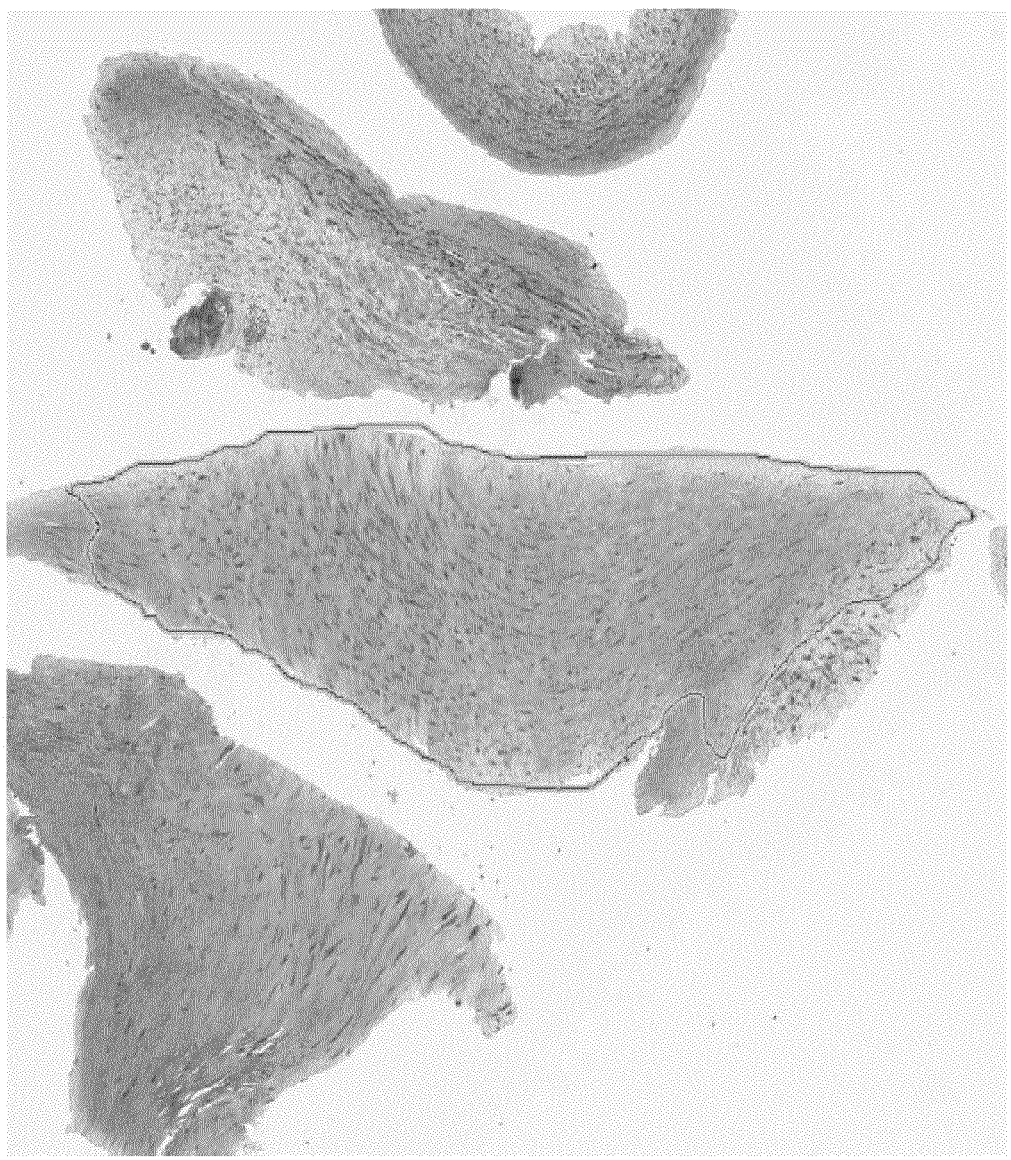
FIG. 2 shows an example of fibrocellular tissue.

Fibrocellular: Fibrocellular plaque tissue was consisted of moderate amount of connective tissue and intermediate numbers of smooth muscle cells (FIG. 2).

Figure 3:
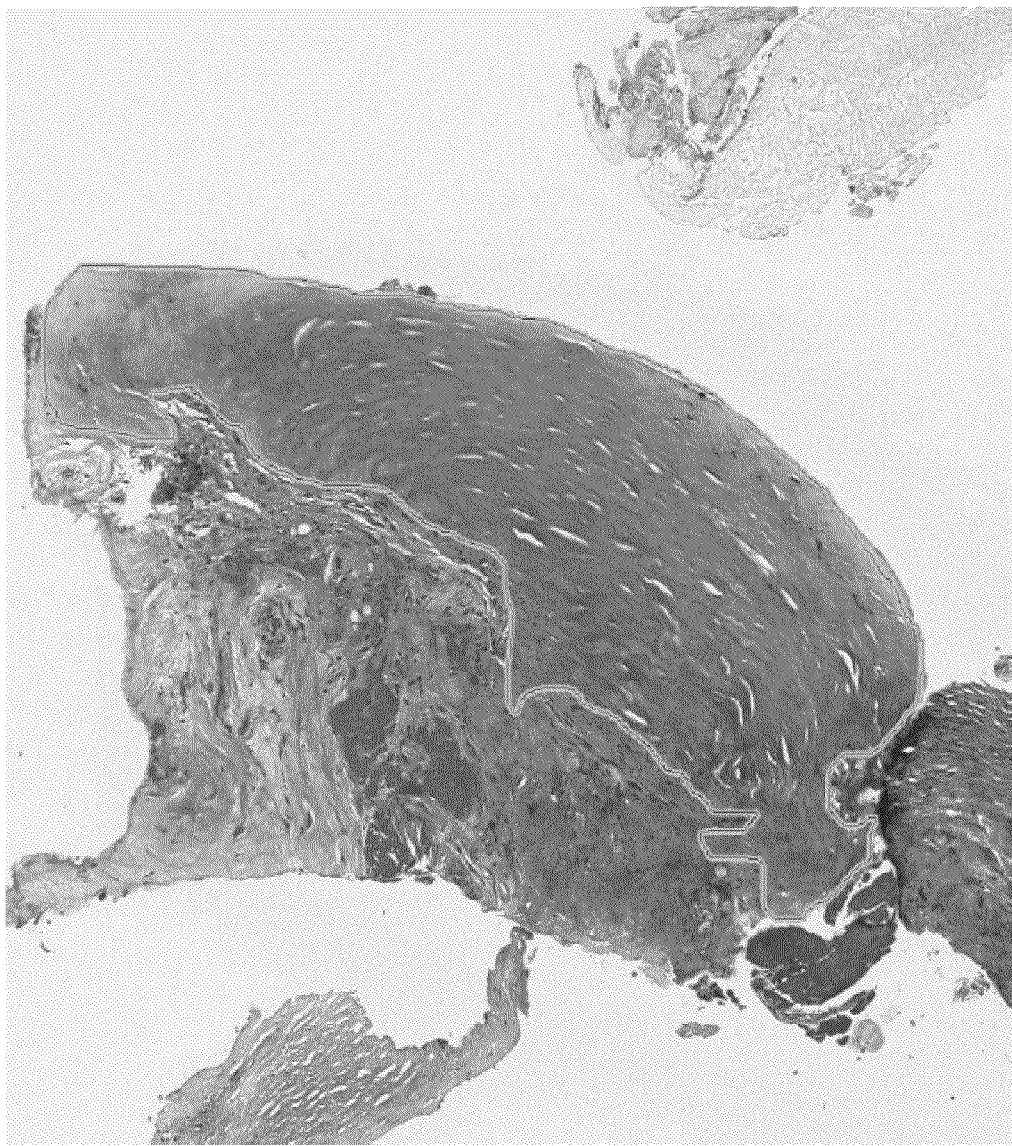
FIG. 3 shows an example of fibrous tissue.

Fibrous: Fibrous plaque tissue was defined by presence of abundant dense connective tissue with sparse cells (FIG. 3).

Figure 4:
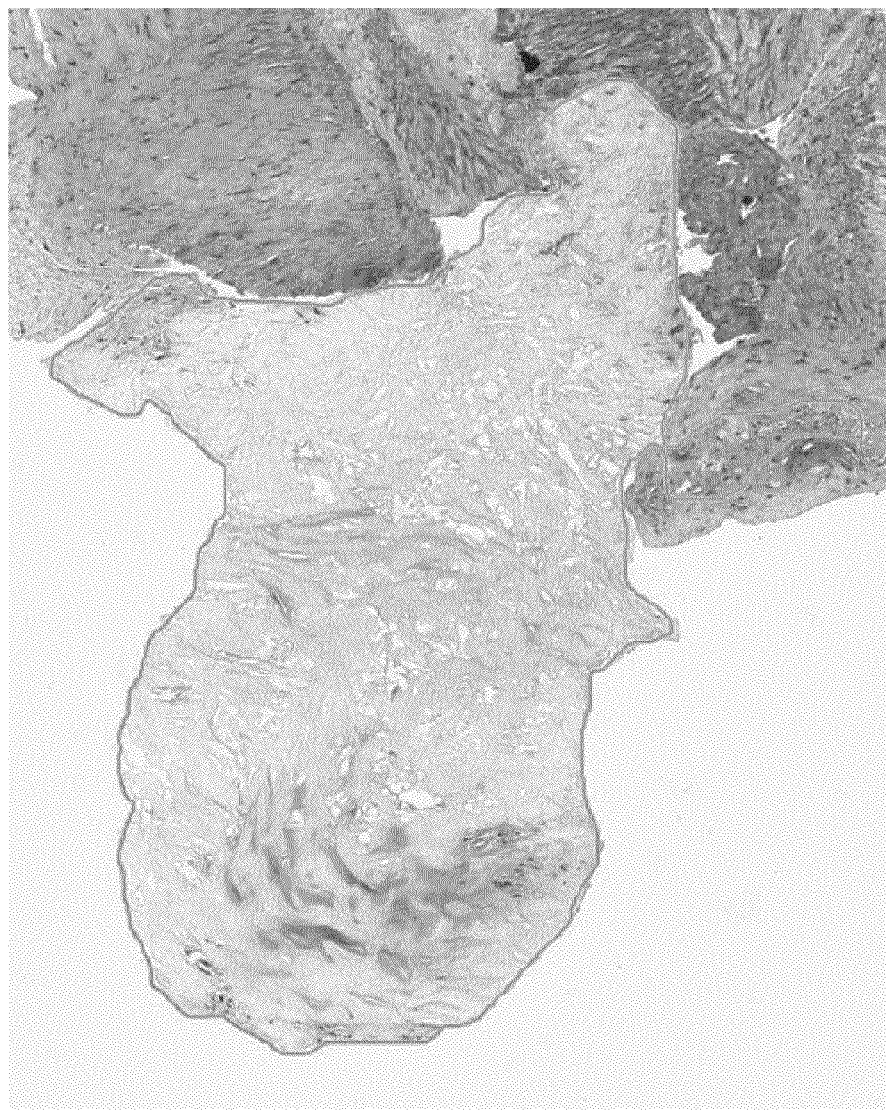
FIG. 4 shows an example of a lipid-rich region of tissue.

Lipid-rich: Lipid rich lesion was defined as an area of amorphous materials containing cholesterol crystals, loosely aggregated necrotic debris or collection of foam cells (FIG. 4).

Figure 5:
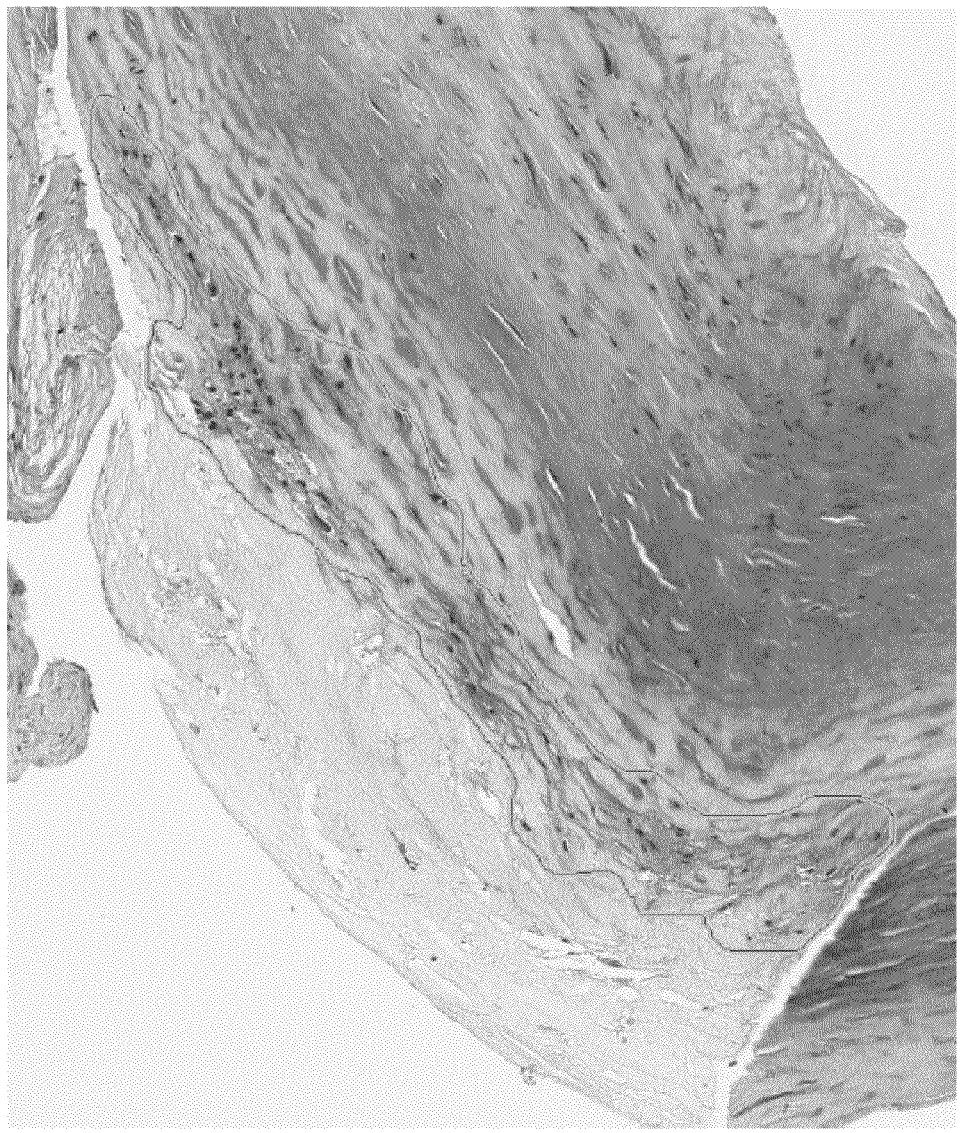
FIG. 5 illustrates a region of tissue containing inflammatory cells.

Inflammatory cells: Inflammatory cell infiltration was evidence by the presence of clusters of macrophages and lymphocytes (FIG. 5).

Figure 6:
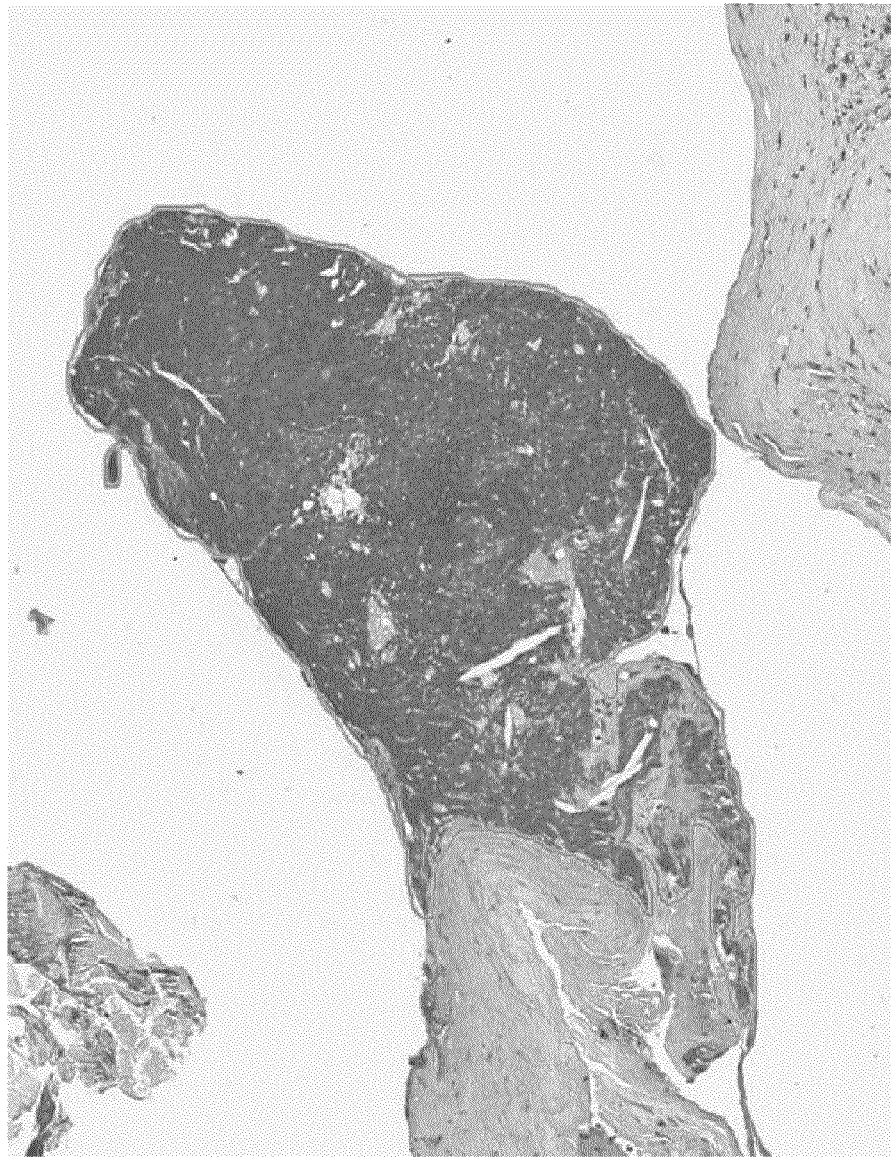
FIG. 6 shows a thrombus.

Thrombus: Thrombus was defined as an organized collection of fibrin, platelets and red blood cells (FIG. 6).

Figure 7:
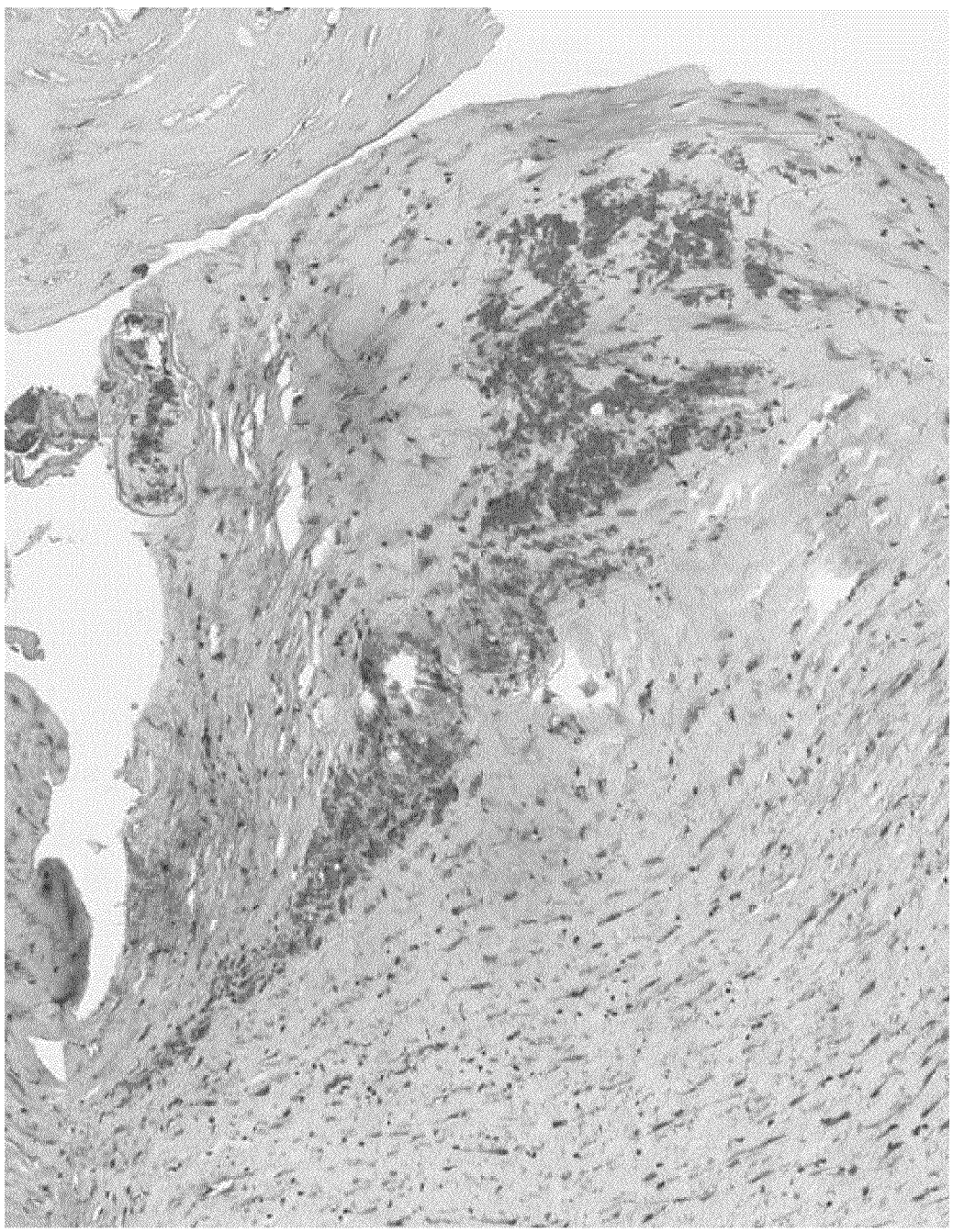
FIG. 7 shows an example of a hemorrhage.

Hemorrhage: Hemorrhage was defined as collections of erythrocytes within plaque matrix that were outside of vasa vasorum and that resulted in some distortion of the plaque structure (FIG. 7).

Figure 8:
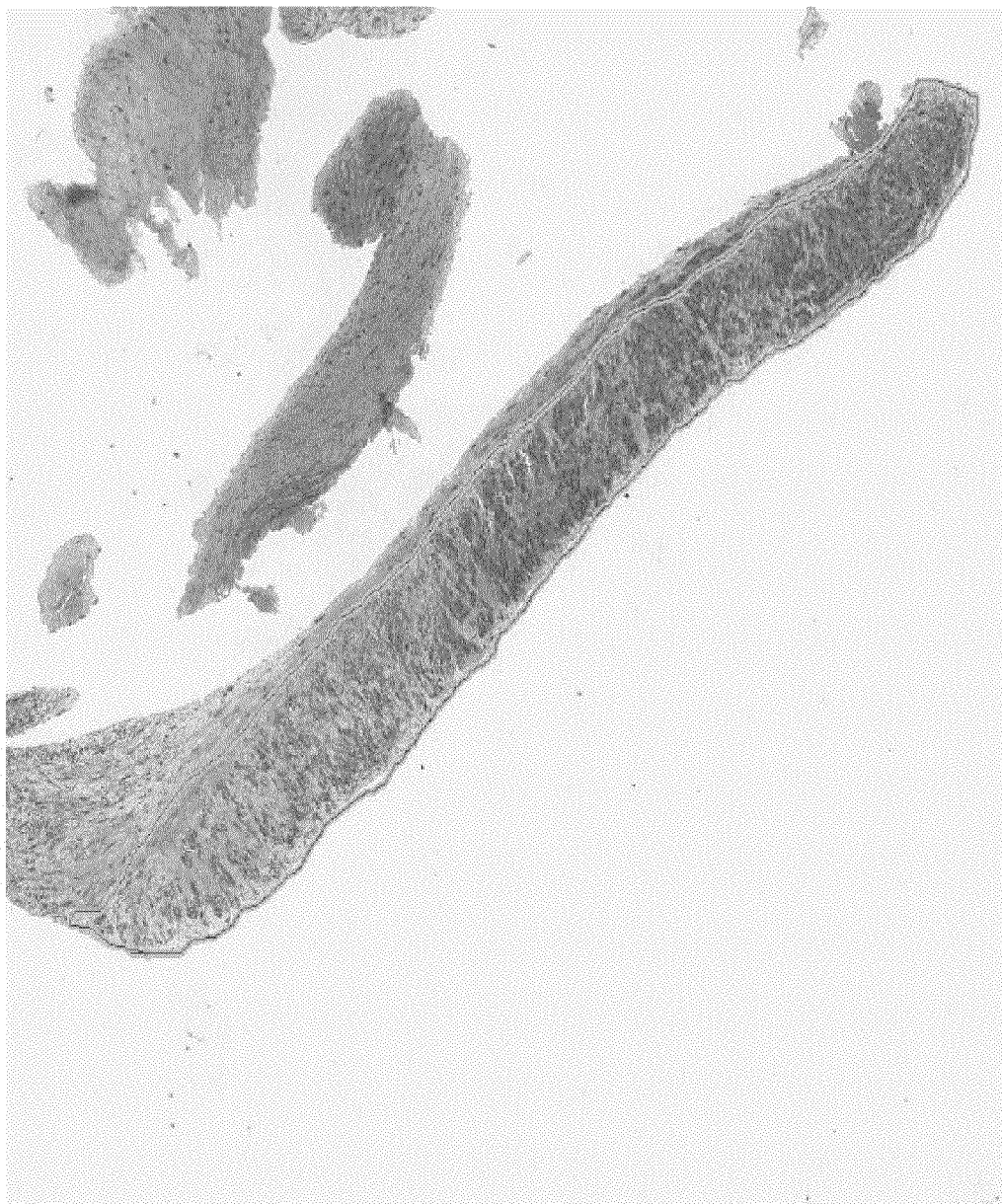
FIG. 8 illustrates the media portion of arterial tissue.

Media: Media was recognized by the presence of internal elastic membrane and more orderly smooth muscle cells and connective tissue matrix (FIG. 8).

Figure 9:
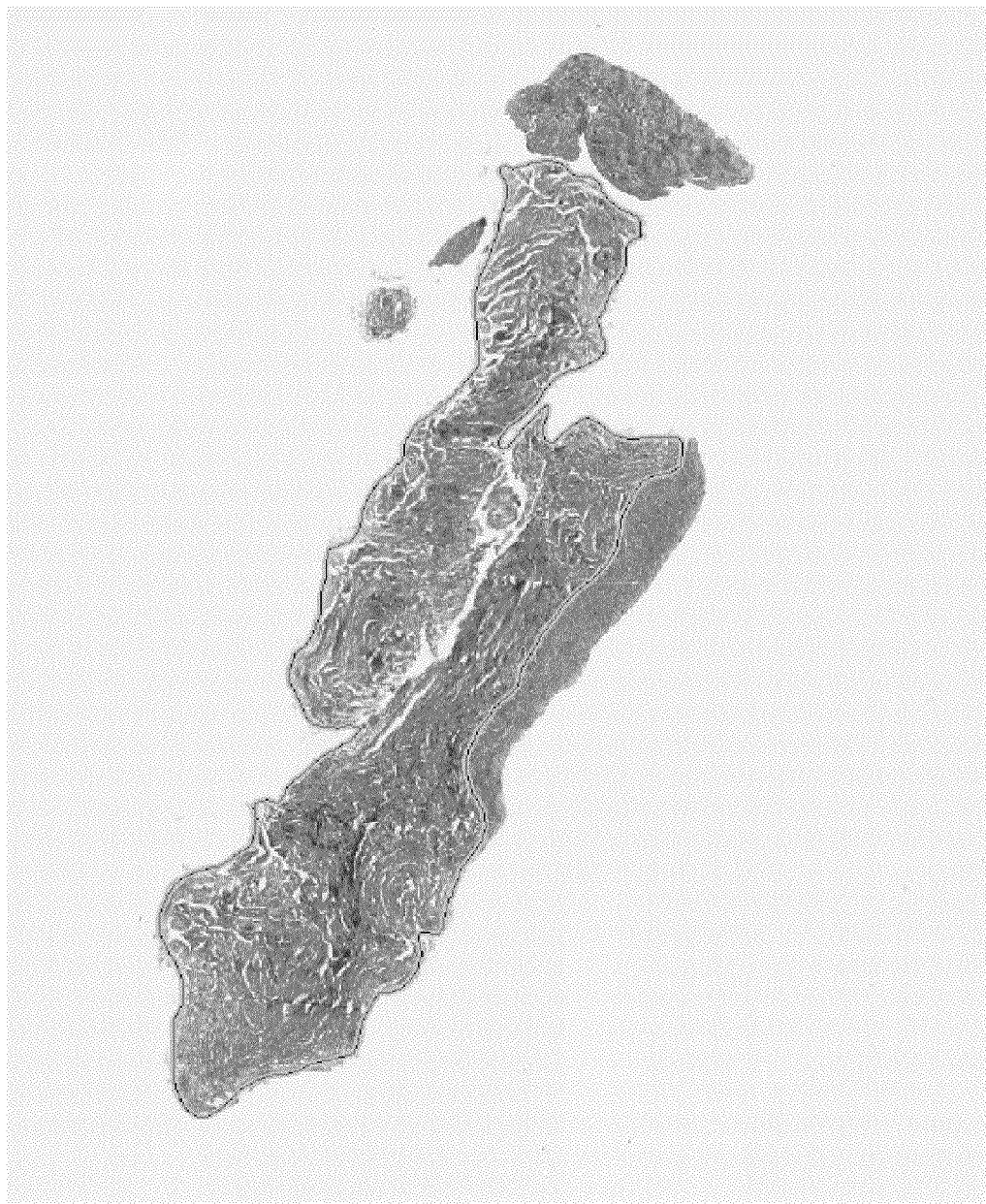
FIG. 9 shows a portion of adventitia tissue.

Adventitia: Adventitia was defined as a vessel layer consisted of coarse fibrous connective tissue bundles with fragments of external elastic membrane, and some times, admixed small blood vessels or nerves (FIG. 9).

Figure 10:
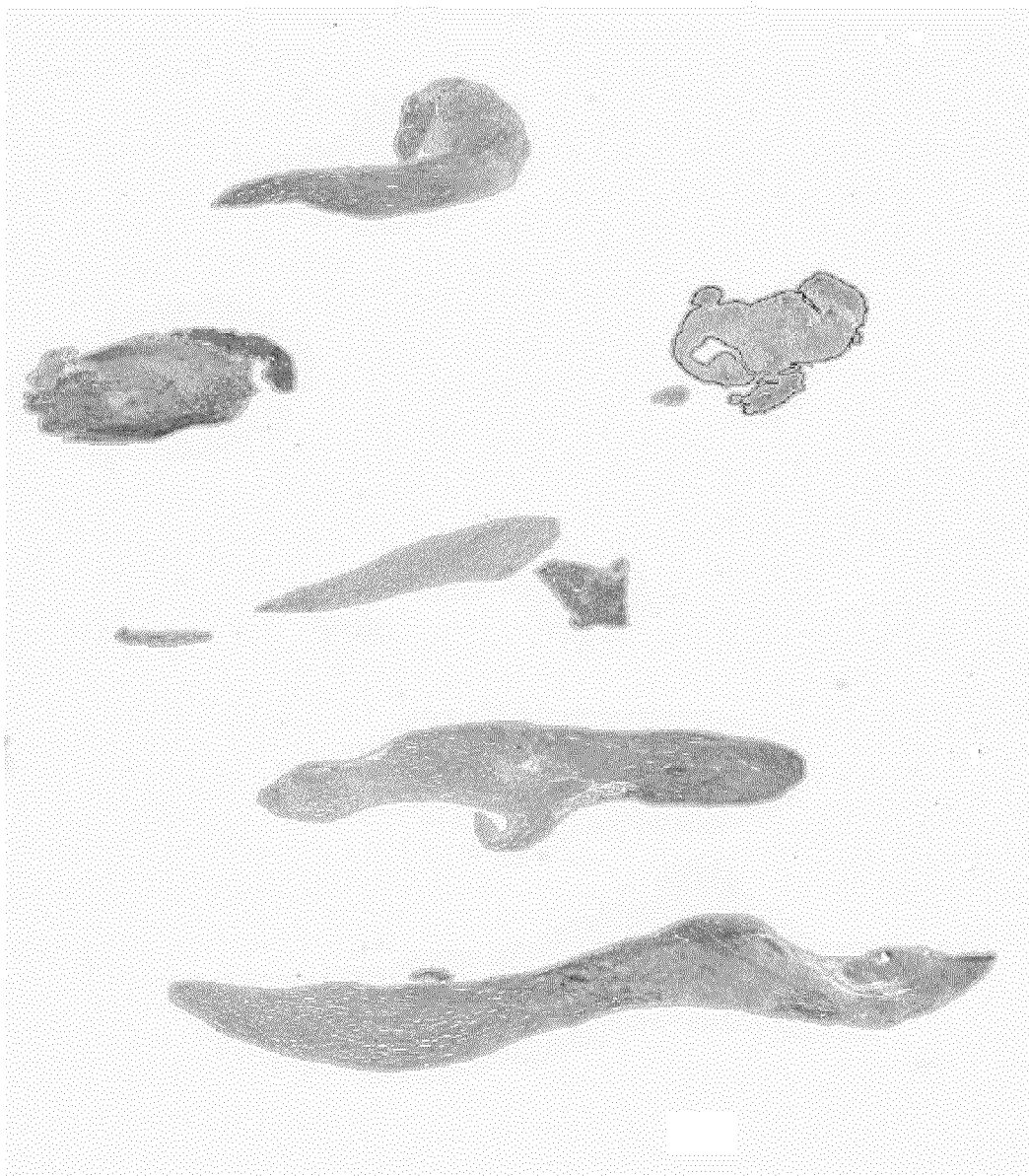
FIG. 10 shows an example of a total section area.

Evaluation and Quantification of Histological Elements Atherosclerotic Plaque Tissue in Digital Images The digital images were reviewed to define different histological components in the section. ScanScope computer analysis tools were used to draw boundaries around each tissue fragment and measure total section area on the digital slide (FIG. 10). Individual histological component was marked to calculate each element area (FIGS. 1~9). The individual component area was then divided by the total section area to calculate individual percentage for each component. From these measurements, a quantitative histological dataset was built to include total section area, individual component area, and percentage of each element for every specimen.

Quantitative Histology and its Clinical Relevance

The quantitative histology data were combined with clinical and angiographic follow-up information to analyze the relation between individual histology component and clinical outcome after directional atherectomy procedure.

Analysis

Tissue taken from all of the 825 patients (approximately 4000 specimens) was examined as described above. The analysis was performed without any knowledge of the patient outcomes. As part of the analysis, the criterion above were used to quantify the areas of cellular hyperplasia, media, media and adventitia, thrombus and hemorrhage, lipid and inflammatory cells, unidentified fibrocellular, and fibrous tissue, by individually inspecting and drawing the area around each component on over 4000 specimens. The total section area was measured by computer and these values were used to calculate the individual percentages for each component. A summary of the measured components appears in Table 1, below. All variables ending with mm² represent the area measurements in square mm while variables ending with area are expressed as percentages of the total section area (for example, for the 825 slides available the square mm of fibrous area (fibareamm2) averaged 3.18 mar and the total section area (totalsectionmm2) averaged 9.70 mm² so 33.3% of the total section was fibrous tissue as determined by quantitative histology using this system.

These histological results were matched using the DCA procedure number on the tissue slides with the DCA number on the follow-up records, and merged. The resultant database was used to determine if there were any histological predictors for risk of restenosis in the population combining de novo and restenosis lesions. The analysis was repeated for patients who had not had a previous procedure (de novo lesions) and repeated for those patients who had been previously treated (restenosis lesions.).

TABLE 1

| Variable | Obs | Mean | Std. Dev. | Min | Max |
|---|---|---|---|---|---|
| fibarea | 825 | .3331044 | .2082072 | 0 | 1.2124 |
| fibareamm2 | 825 | 3.184831 | 3.075813 | 0 | 21.1463 |
| fibrocellu~a | 825 | .4207189 | 1.364847 | 0 | 39.33 |
| fibrocellu~2 | 825 | 3.557204 | 2.840935 | 0 | 20.8931 |
| hyperarea | 825 | .1404861 | .1890572 | 0 | .8378 |
| hyperareamm2 | 825 | 1.492413 | 2.889506 | 0 | 33.7809 |
| lipidinfla~a | 825 | .0613177 | .0835959 | 0 | .6168 |
| lipidinfla~2 | 825 | .6174668 | .9705671 | 0 | 7.4283 |
| mediaadven~a | 825 | .0151333 | .0513151 | 0 | .7157 |
| mediaadven~2 | 825 | .1342177 | .3881693 | 0 | 3.4761 |
| mediaadven~m | 825 | .4599795 | 1.265656 | 0 | 11.9982 |
| mediaarea | 825 | .0305399 | .0611516 | 0 | .5539 |
| mediaareamm2 | 825 | .2798194 | .5173945 | 0 | 4.3514 |
| medialengt~m | 825 | 1.644731 | 2.626461 | 0 | 18.3675 |
| medialengt~2 | 825 | .1936225 | .3852916 | 0 | 4.45 |
| thromhemoa~a | 825 | .0483193 | .1023152 | 0 | 1 |
| thromhemoa~2 | 825 | .4376082 | 1.02324 | 0 | 8.2718 |
| totalsecti~2 | 825 | 9.703561 | 7.047 | .1943 | 56.0936 |

As expected the best predictor of reduced risk of restenosis was the post interventional minimal lumen diameter (UM). The larger the lumen that was achieved at the end of the intervention the lower the restenosis rate (Baim and Kuntz bigger is better theory).

For the 825 patients with saved slides, clinical and follow-up quantitative angiography was available for 692 (83.3%) of the patients. Using QCA the angiographic restenosis rate was 39.6% (all pts), 37.5% (de novo pts) and 42.0% (restenosis pts).

Univariant analysis using Student's t-test showed that there was an increased incidence of restenosis in de novo lesion comparing the presence or absence of hypercellular plaque measured quantitative histology. For de novo patients with hypercellular plaque present in the histology the restenosis rate was 45% vs. 30% when hypercellular plaque was absent. P=0.0019. This association became even more pronounced when lipid and inflammatory cells were present. In patients with de novo lesions that had both hypercellular plaque as well as lipid and inflammatory cells the restenosis rate was 50% compared to 28% when both lipid/inflammatory cells and hypercellular plaque were not present.

Stepwise logistic regression was then used to compare MLD post intervention to the quantitative histological parameters seeking to determine if any of the histology findings were independent predictors of restenosis in the de novo patient population. MLD post (p=0.000) and hypercellularity expressed as a % of total section area (p=0.012) were both independent predictors of restenosis. The % of tissue represented by media/adventitia (p=0.317), lipid/inflammatory cells (p=0.881) and thrombus/hemorrhage (p=0.394) were not independent predictors of restenosis, as indicated in Table 2, below:

TABLE 2

Iteration 0: log likelihood = −250.22451
Iteration 1: log likelihood = −236.74983
Iteration 2: log likelihood = −236.45296
Iteration 3: log likelihood = −236.45208

TABLE 2-continued

| | | | | | | |
|---|---|---|---|---|---|---|
| Iteration 4: log likelihood = −236.45208 | | | | | | |
| Logit estimates | | | | Number of obs = | | 377 |
| | | | | LR chi2(2) = | | 27.54 |
| | | | | Prob > chi2 = | | 0.0000 |
| Log likelihood = −236.45208 | | | | Pseudo R2 = | | 0.0550 |
| rsatfup | Coef. | Std. Err. | z | P > \|z\| | [95% Conf. Interval] | |
| postmm | −.6996334 | .1745044 | −4.01 | 0.000 | −1.041656 | −.357611 |
| hyperarea | 2.422905 | .9602835 | 2.52 | 0.012 | .5407841 | 4.305026 |
| Lipidinfla~a | −.1721168 | 1.151897 | −0.15 | 0.831 | −2.429794 | 2.08556 |
| mediaadven~a | −2.131326 | 2.128189 | −1.00 | 0.317 | −6.302499 | 2.039848 |
| thromhemoa~a | .8373006 | .9829864 | 0.85 | 0.394 | −1.089317 | 2.763919 |
| _cons | 1.194915 | .4874256 | 2.45 | 0.014 | .238978 | 2.149651 |

When the analysis was repeated for those de novo patients with both lipid/inflammatory cells and hypercellularity the predicative value of quantitative histology increased, Stepwise logistic regression showed the relationship between quantitative histological evidence of hypercellularity and restenosis at 6-9 month follow-up to be more significant for both MLD post and hypercellular % area (p=0.001 for both), as illustrated in Table 3.

TABLE 3

| | | | | | | |
|---|---|---|---|---|---|---|
| Iteration 0: log likelihood = −180.79407 | | | | | | |
| Iteration 1: log likelihood = −167.91003 | | | | | | |
| Iteration 2: log likelihood = −167.6878 | | | | | | |
| Iteration 3: log likelihood = −167.68732 | | | | | | |
| Logit estimates | | | | Number of obs = | | 269 |
| | | | | LR chi2(2) = | | 26.21 |
| | | | | Prob > chi2 = | | 0.0000 |
| Log likelihood = −167.68732 | | | | Pseudo R2 = | | 0.0725 |
| rsatfup | Coef. | Std. Err. | z | P > \|z\| | [95% Conf. Interval] | |
| postmm | −.6572298 | −.2050497 | −3.21 | 0.001 | −1.05912 | −.2553398 |
| hyper-area | 4.720442 | 1.38667 | 3.40 | 0.001 | 2.002619 | 7.438266 |
| _cons | 1.022995 | −.5513755 | 1.86 | 0.064 | −.0576811 | 2.103671 |

These findings confirm that MLD post was an independent predictor of restenosis in the de novo patient population (as expected). However, the finding that quantitative histology provides a new parameter as an independent predictor of restenosis is surprising. When quantitative histology confirms the presence of both hypercellularity and lipid/inflammatory cells, this combination is as powerful as MLD post as an independent predictor of restenosis. Unexpectedly, quantitative histology may provide a new parameter as an independent predictor of restenosis. Based on these findings, when quantitative histology confirms the presence of both hypercellularity and lipid/inflammatory cells, this combination is as powerful as MLD post as an independent predictor of restenosis.

This new finding is not dependent on classical histological techniques, such as those used above. Using light microscopy and routine histological staining may take several days and may be of limited value in helping drive decisions on patient treatment during an actual procedure. Thus, described briefly in Section II below are systems for providing real-time tissue characterization with the resolution approaching that of light microscopy that allow or provide tailored therapies directed toward the biology of the lesion. For example, in some variations, Optical Coherence Tomography may be used, although the general methods and applications described herein are not limited to any particular modality.

Section II: Applications

A system (e.g., a system for treating atherosclerosis) may be provided that is configured to allow visualization (direct imaging) or an indicator of one or more of any of the factors described above. In a particular, a system may be configured to provide visualization or an indication of hypercellularity, lipid-rich tissue regions, and/or inflammatory cells. In some variations the system may provide an index of one or more of these factors, or a "restenosis index" based on one or more of these factors. In some variations, the system may provide an image of a tissue region (e.g., a peripheral vessel) that allows visualization of one or more of hypercellularity, lipid-rich tissue and/or inflammatory cells. The system may be configured so that multiple versions of the same image are displayed that are specific for showing one or more of these factors. The system may also include logic that assists the user in identifying or quantifying these factors.

In one example, a system for treating atherectomy includes one or more visualization modalities that permit visualization one or more of these factors. For example, an optical coherence tomography (OCT) imaging modality may be used. OCT may therefore provide real-time data indicating, for example, multicellularity, lipid content and/or inflammatory cells. An OCT system may be configured to use one or more wavelengths of light (or a band or mixture of wavelengths) that is selective for one or more of these features. Any of the imaging systems described herein (including OCT) may be used in conjunction with one or more markers (e.g., vital dyes, contrast agents, etc.) to help visualize. In some variations, the OCT may be used in vivo prior to excising the tissue. In other variations, the tissue may be examined as (or shortly after) it is removed from the vessel. Thus, any of the systems described herein may include an atherectomy device such as an atherectomy catheter. In some variations, the catheter may be guided or controlled based in part of the feedback or guidance from the determination/visualization of one or more of the factors described herein. For example, regions of the tissue exhibiting hypercellularity may be excised more completely or aggressively than other stenotic regions, or may be treated by stenting and/or the application of a local drug agent.

Preliminary analysis of human cadaver coronary artery tissue by OCT compared to a routine light microscopic image of the same vessel at the same site suggests that OCT may be configured to distinguish the lipid and fibrous components. OCT variations that may be used include OCT systems having multiple fibers, polarization OCT imaging, multiple/selectable wavelength, birefringence imaging using OCT, combinations of OCT imaging with ultrasound or other tissue-perturbation techniques, or the like. For example, OCT may be used to examine the elastic properties of the tissue which may correspond to the lipid content. Perturbing (e.g., vibrating) the tissue either directly (mechanically by pushing against the tissue, including inflating a balloon against a region of the tissue and imaging it) or using ultrasound (to vibrate the tissue) may indicate the lipid composition of the tissue region.

Figure 12:
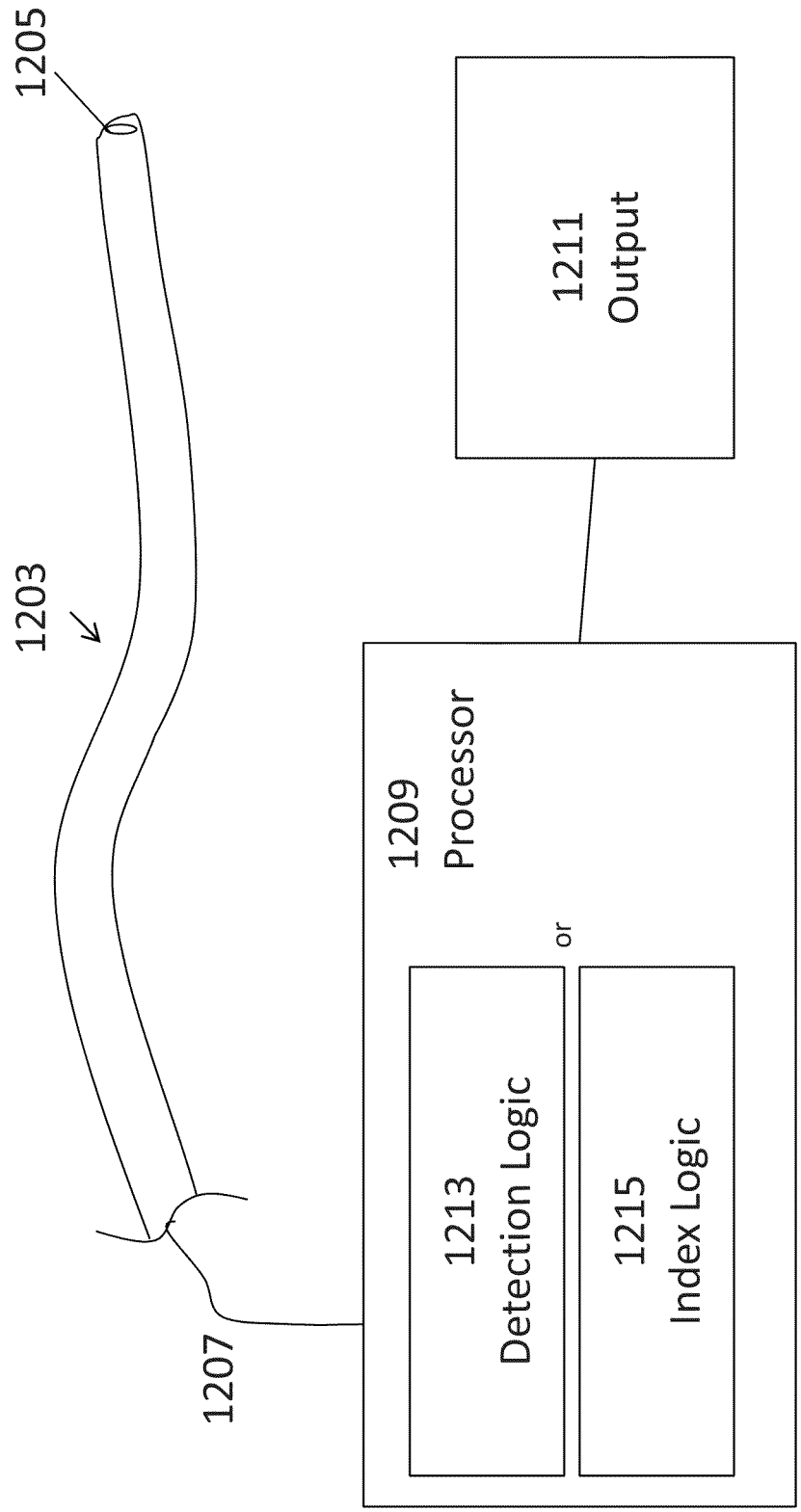
FIG. 12 schematically illustrates one variation of a system for determining the risk of restenosis as described herein.

For example, FIG. 12 shows a schematic diagram of one variation of a system (which may also be integrated in a device) for determining the risk of restenosis. In this example, the system/device includes a catheter 1203 using an OCT imaging modality 1205, including a lensing region 1205 at the distal end from which light may exit the side of the catheter for examining a region of arterial wall. The system also includes a processor 1209 connected 1207 to receive images from the OCT subsystem (not shown). The processor may be configured to include or execute detection logic 1213 and/or index logic 1215 to measure, estimate or otherwise determine the extent of hypercellularity and one or both of lipid-richness and/or the presence of inflammatory cells. The system may also include an output 1211, such as a monitor, display, or the like. The output may display the image of the arterial wall (or multiple images) as well as display or indicate regions of hypercellularity and/or regions of high lipid-richness and/or the inflammatory cells. In some variations the display shows only region of high-risk for restenosis. The display may be adjustable, and allowing the threshold to adjust the level of risk of restenosis (e.g., changing a threshold above or below which regions of high/low indexes for restenosis are shown).

Other imaging modalities that may be used with the systems described herein, either alone or in combination, may include ultrasound, angiography (e.g., QVA), CT, MRI, SPECT, PET/CT, X-ray, etc. Virtually any imaging modality may be used, particularly those that may provide images of vessel regions displaying hypercellularity, lipid-rich tissue, and/or inflammatory cells.

Indication of the hypercellularity, lipid rich tissue, inflammatory cells and/or other factors may be provided in real time, near-real time, or otherwise during the procedure, as mentioned above. "Near-real" time may refer to a slight delay (e.g., time delayed images) compared to strict real time; for example an image in near-real time may lag by a few seconds or minutes. In some variations images illustrating the stenosed tissue regions may be saved for later analysis. In still other versions the tissue may be removed before the analysis, and correlated with a particular region, or merely with a particular patient. For example, an atherectomy device may be used to remove the tissue, which can then be examined (including by staining, fixation, or other treatments not typically advocated before removal from the patient) for these factors.

Any of the systems described herein may be configured to provide automated analysis of these factors. For example, a system for treating atherosclerosis may include logic for analyzing images of the vessel and determine an index of one or more of hypercellularity, lipid-rich membrane, and/or inflammatory cells. An index may be quantitative (e.g., a percentage, or percentage area, or square or cubic area or density). The index may be qualitative (e.g., "high", "medium", "low", etc.). An index for the risk of restenosis may also be provided, based on the predictive risks described above. For example, an index of restenosis may be provided based (weighted heavily) on the degree or extent of very active (e.g., hypercellularity) tissue when there is a significant increase in lipid-rich tissue and/or inflammatory cells. Thus, in some variations, the system may include image analysis logic configured to examine one or more of the features described above.

Logic (e.g., indexing or detecting logic) may include computer-executable code (software), hardware, firmware, or any combination of these. For example, detection and/or index logic may be executable on or as part of a computer processor (e.g., microprocessor) that is either a general-purpose processor, a distributed processor, or a dedicated processor (or processors).

In some variations the system provides images that are colored, highlighted, or otherwise marked to indicate regions displaying some threshold (typically correlating to an enhanced risk for restenosis) based on one or more of the factors described herein. Multiple images may be displayed and/or marked, Or a single composite (e.g., "high risk" for restenosis) image may be provided.

Figure 11:
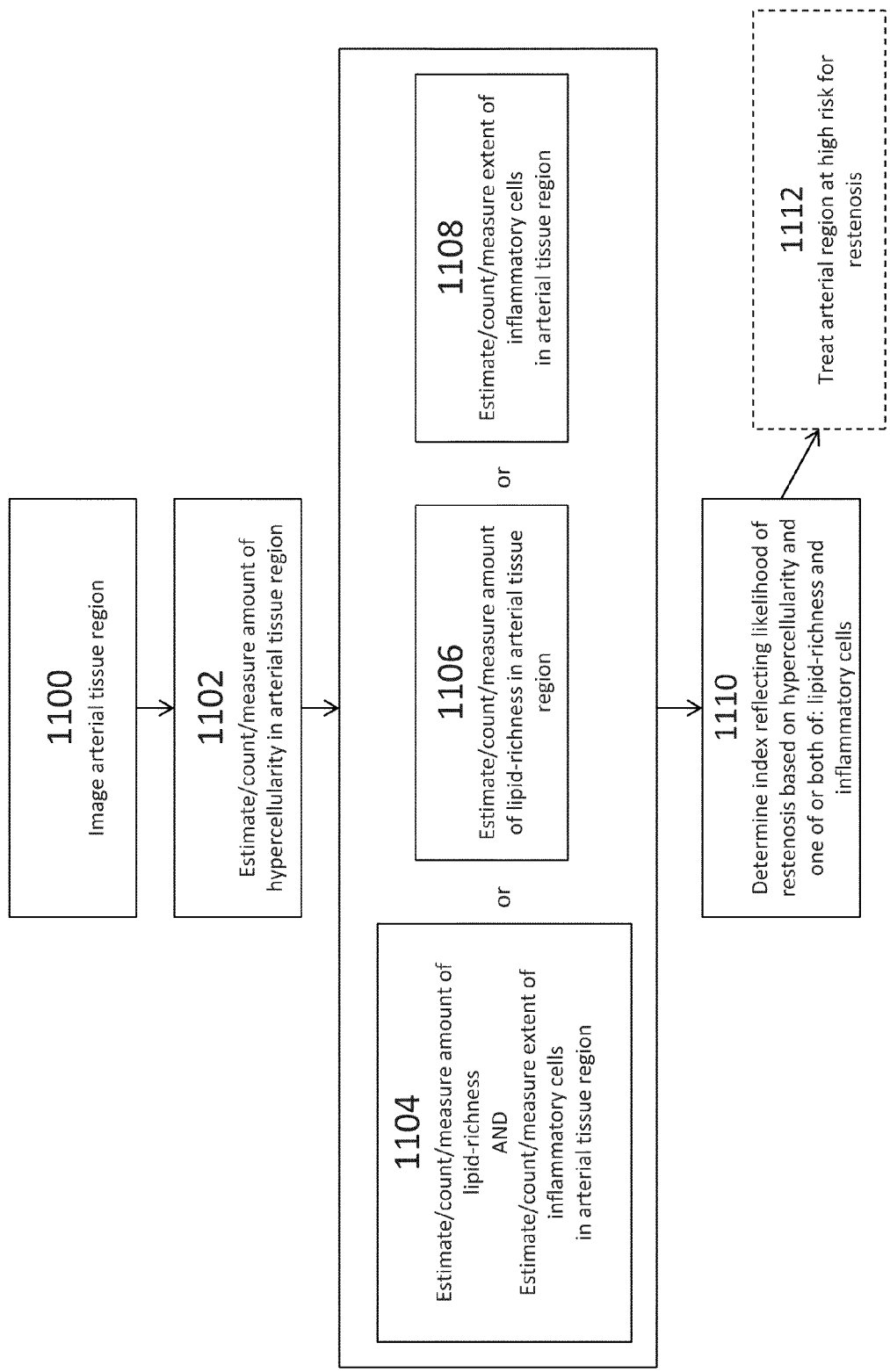
FIG. 11 is a diagram schematically illustrating one method of determining the risk of restenosis.

Also described herein are methods of determining a risk of restenosis and methods of treating atherosclerosis. FIG. 11 illustrates one variation of a method determining (and treating) restenosis.

In general, a method of determining a risk of restenosis as described herein may include the steps of determining from the tissues of a vessel if the tissue is hypercellular. The method may also include determining if the tissue is lipid-rich and/or the extent of inflammatory cells in the tissue. Determining if the tissue is hypercellular, lipid-rich and/or the extent of inflammatory cells may include determining a quantitative measure of the extent of hypercellularity, lipid-rich tissue and/or the extent of inflammatory cells. The tissue may be visualized and these determinations may be made by a visual means, or the determinations may be made without presenting an image of the tissue.

Determining if a tissue is hypercellular may also include determining the density of cells per unit area, or the density of a marker for cells (e.g., nuclei, cell membranes, etc.). As mentioned above, a determination of hypercellular tissue may mean simply presenting an image of the tissue in a modality that allows visualization of hypercellular tissue. For example, determining if a tissue is hypercellular may mean displaying an OCT image taken with a wavelength or plurality of wavelengths that permit visualization of hypercellularity (or a birefringent image, a polarized OCT image, etc.). Regions of relative hypercellularity may be marked or unmarked on the image. Similarly, determining if a tissue is lipid-rich may mean simply displaying an image of tissue that shows the relative lipid-richness of the tissue, which may be marked or unmarked on the image; determining the extent of inflammatory cells may mean showing an image of a tissue in which it is possible to detect inflammatory cells (or one or multiple types).

In some variations, the determination steps described may include adding a marker, dye, or indicator of the factor to be evaluated (e.g., cellularity, lipid content, inflammatory etc.). The determining step may also include perturbing the tissue so that the factor to be evaluated may be more readily determined using a particular methodology that benefits from this perturbation (e.g., by changing the temperature of the tissue, by vibrating the tissue, by irradiating the tissue, etc.).

For example, in FIG. 11, the method includes the steps of imaging a region of arterial tissue (e.g., arterial wall tissue or a depth through a region of arterial wall) 1100. This region is then examined to determine the extent of hypercellularity (e.g., estimating/counting/measuring the extent of hypercellularity) 1102. The same region is examined to determine either: (1) the extent of lipid-richness 1106; (2) the presence of inflammatory cells 1108; or (3) both 1104. From these estimates (1102 and 1108, 1105 or 1104) an index reflecting the likelihood of restenosis may be determined 1110. Optionally, if the risk of restenosis in this region of the artery (e.g., the region adjacent to the tissue examined) is sufficiently high, then the tissue may be treated to prevent restenosis or to mitigate the effects of restenosis 1112. As described herein, the magnitude of the index of restenosis may be used to predict the likelihood of restenosis. For example, one or more thresholds (e.g., confidence intervals) may be determined for comparison to the index to predict restenosis. These confidence intervals and/or thresholds may be determined experimentally (e.g., from population studies) or theoretically, e.g., extrapolated from data such as that shown herein.

Methods of determining a risk of restenosis may also include determining an index of restenosis based on the determination of one or more of the factors mentioned herein, including hypercellularity, lipid content, and/or inflammatory cells. In some variations the index may be presented for the patient as a whole (a global index) or for specific regions mapped to the patients anatomy (e.g., within the vessels). Thus, a method of determining a risk of restenosis my be present as an image or series of images of the subject's vessel lumen, indicating regions of greater and/or lesser risk. Any of the imaging modalities described herein may be used in the determining steps mentioned above.

In some variations, the methods of determining the risk of restenosis may also include the step of inserting a device configured to help determine the risk of restenosis (e.g., a catheter, probe, etc.) within the vessel. Alternatively, in some variations, the method may include determining the risk non-invasively, using one or more imaging modalities from outside of a patient.

As mentioned, any of the methods described herein typically include the step of determining if a tissue (e.g., peripheral vascular tissue) is one or more of hypercellular, lipid-rich and/or includes inflammatory cells. Any of these determining steps may also include determining the extent to which the tissue is hypercellular, and/or includes in inflammatory cells. For example, a measure of hypercellular, lipid-richness and/or density of inflammatory cells may be compared to a standard or metric for these factors, based on the experimental data described above. The measure may be +/– some percentage of a threshold value (e.g., within +/–1%, 2%, 3%, 5%, 10%, 15%, 20%, 25%, 30%, 50%, etc. of a threshold value indicated from the experimental data).

A method of treating atherosclerosis typically includes the step of determining if a tissue (e.g., peripheral vascular tissue) is one or more of hypercellular, lipid-rich and/or includes inflammatory cells as mentioned above. This (these) determining steps may include any of the variations described above. The method of treating atherosclerosis may also include the step of removing tissue from the vessel. This removing step may be performed before, during or after the determining step(s).

In some variations, the method of treating atherosclerosis also includes the step of treating regions of the vessel that have a higher risk for restenosis (as suggested by the determination of one or more of hypercellularity, lipid richness and/or inflammatory cells) more aggressively than regions of lower risk. For example, regions of de novo atherectomy lesions having a higher hypercellularity and/or risk of restenosis may be treated with a drug eluting stent while atherectomy alone or atherectomy with a bare metal stent could be advised for less cellular lesions.

In some variations, the method of treating atherosclerosis may include the step of providing a pharmacological agent if it is determined that the subject is at greater risk for restenosis. For example, based on a subject's overall risk of restenosis, the subject may be given anticoagulants (e.g., clopidogrel (Plavix), etc.), or drugs that prevent excessive cell division (e.g., within the lumen), or the like.

The data describe above may also be interpreted to suggest that good results may be achieved by getting the best possible luminal gain with any intervention (atherectomy, stent, etc.) even to the extent of resecting media and adventitia with atherectomy, as long as the vessel is not perforated. Media and adventitia in the quantitative histology was not associated with an increased risk of restenosis, and a trend toward reduced restenosis was seen when media was present ($p=0.107$) in the extracted tissue. These data may support the concept that the cellularity of a de novo lesion is an important predictor or restenosis intervention. Thus any of the methods described herein that could maximize luminal gain, avoid perforation, and characterize the underlying tissue would be very desirable to reduce restenosis, either locally (e.g., at regions of greater risk for restenosis or in patients at higher risk) or globally. Overall a determination of the risk of restenosis may be useful to help guide the aggressiveness of the treatment.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for determining an enhanced risk of restenosis in an arterial tissue, the device comprising:
    an imaging catheter having a sensor configured to image a portion of an artery;
    a processor configured to receive images of the artery from the sensor and to detect regions of hypercellularity in the artery by counting or estimating the amount of satellite-to-spindle shaped smooth muscle cells within stroma in the received images, and further configured to detect regions of either or both: lipid-rich tissue and inflammatory cells in the artery from the received images; and
    a display configured to display a modified view of the artery indicating hypercellularity and the one or both of lipid-rich tissue and inflammatory cells in the artery.

2. The device of claim 1, wherein the imaging catheter is an atherectomy catheter.

3. The device of claim 1, wherein the imaging catheter is an OCT imaging catheter and the sensor comprises an OCT imaging sensor.

4. The device of claim 1, wherein the processor and display are configured to operate in real or near-real time.

5. The device of claim 1, wherein the processor comprises detection logic configured to detect the regions of hypercellularity and either or both: lipid-rich tissue and inflammatory cells in the artery from the received images.

6. The device of claim 1, wherein the display is configured to highlight region of overlap indicating both hypercellularity and either or both: lipid-rich tissue and inflammatory cells in the artery on the modified view of the artery.

7. The device of claim 1, wherein the processor further comprises index logic configured to determine an index of restenosis based on the degree of hypercellularity and either or both: the degree of lipid-rich tissue and the degree of inflammatory cells in the artery from a region of the artery in the received images.

8. The device of claim 7, wherein the index logic determines the index of restenosis based on the degree of hypercellularity, the degree of lipid-rich tissue and the degree of inflammatory cells from the region of the artery.

9. The device of claim 7, wherein the display is configured to display the index of restenosis for the region.

10. The device of claim 7, wherein the display is configured to overlay an indicator of the index of restenosis for the region over a view including the region of the artery.

11. A system for indicating an enhanced risk of restenosis in an arterial tissue, the system comprising:
an imaging modality configured to image a region of arterial tissue; and
a processor configured to receive the image of the region of arterial tissue from the imaging modality and to determine a measure of hypercellularity by counting or estimating the amount of satellite-to-spindle shaped smooth muscle cells within stroma and further configured to determine one or both of: a measure of how lipid-rich the tissue region is and a measure of how many inflammatory cells there are associated with the tissue region; and
index logic configured to determine an index of restenosis for the tissue region based on the measure of hypercellularity and one or both of the measures of how lipid-rich the first tissue region is and the measure of how many inflammatory cells are associated with the first tissue region.

12. The system of claim 11, further comprising an output configured to output the index of restenosis.

13. The system of claim 11, further wherein the index logic is configured to determine an index of restenosis based on the measure of hypercellularity, the measure of how lipid-rich the first tissue region is, and the measure of how many inflammatory cells are associated with the first tissue region.

14. A method of determining an enhanced risk of restenosis in an arterial tissue, the method comprising:
determining a measure of hypercellularity in a first arterial tissue region by counting or estimating the amount of satellite-to-spindle shaped smooth muscle cells within stroma;
determining one or both of: a measure of how lipid-rich the first tissue region is and a measure of how many inflammatory cells there are associated with the first tissue region;
determining an index of restenosis for the first tissue region based on the measure of hypercellularity and one or both of the measures of how lipid-rich the first tissue region is and the measure of how many inflammatory cells are associated with the first tissue region; and
presenting the index of restenosis for the first tissue region.

15. The method of claim 14, wherein the step of determining an index of restenosis comprises determining the index of restenosis for the first tissue region based on the measure of hypercellularity and the measure of how lipid-rich the first tissue region is and the measure of how many inflammatory cells are associated with the first tissue region.

16. The method of claim 14, wherein the step of presenting comprises displaying an image of the first tissue region with a visual indicator of the index of restenosis.

17. The method of claim 14, further comprising imaging the first tissue region with an imaging modality configured to detect hypercellularity.

18. The method of claim 14, further comprising imaging the first tissue region with an imaging modality configured to detect lipid-rich regions.

19. The method of claim 14, wherein the step of determining a measure of hypercellularity comprises imaging the first region with optical coherence tomography.

20. The method of claim 14, wherein the step of determining a measure of how lipid-rich the first tissue region is comprises estimating the amount or degree of amorphous material containing cholesterol crystals, loosely aggregated necrotic debris and foam cells.

21. The method of claim 14, wherein the step of determining a measure of how many inflammatory cells are associated with the first tissue region comprises counting or estimating clusters of macrophages and lymphocytes.

22. The method of claim 14, further comprising treating the tissue with a marker, dye, or indicator.

23. The method of claim 14, further comprising inserting a stent adjacent to the first arterial tissue region when the index of restenosis indicates a greater likelihood of restenosis.

24. The method of claim 14, further comprising removing the first tissue region from a patient.

25. A method of preventing restenosis in an arterial tissue, the method comprising:
determining an index of restenosis for a first arterial tissue region based on a measure of hypercellularity of the first arterial tissue region, the measure of hypercellularity based upon counting or estimating the amount of satellite-to-spindle shaped smooth muscle cells within stroma, and one or both of a measure of how lipid-rich the first arterial tissue region is and a measure of how many inflammatory cells are associated with the first arterial tissue region; and
inserting a stent adjacent to the first arterial tissue region when the index of restenosis indicates a greater likelihood of restenosis.

26. The method of claim 25, further comprising removing tissue from the first arterial tissue region.

27. The method of claim 26, wherein the step of determining an index comprises imaging the first arterial tissue region in real or near-real time.

28. A device for determining an enhanced risk of restenosis in an arterial tissue, the device comprising:
an imaging catheter having a sensor configured to image a portion of an artery;
a processor configured to receive images of the artery from the sensor and to detect regions of hypercellularity in the artery based on a presence of satellite-to-spindle shaped smooth muscle cells within stroma in the received images, and further configured to detect regions of either or both: lipid-rich tissue and inflammatory cells in the artery from the received images; and
a display configured to display a modified view of the artery indicating hypercellularity and the one or both of lipid-rich tissue and inflammatory cells in the artery.

29. A method of determining an enhanced risk of restenosis in an arterial tissue, the method comprising:
determining a measure of hypercellularity in a first arterial tissue region by identifying satellite-to-spindle shaped smooth muscle cells within stroma;

determining one or both of: a measure of how lipid-rich the first tissue region is and a measure of how many inflammatory cells there are associated with the first tissue region;

determining an index of restenosis for the first tissue region based on the measure of hypercellularity and one or both of the measures of how lipid-rich the first tissue region is and the measure of how many inflammatory cells are associated with the first tissue region; and presenting the index of restenosis for the first tissue region.

* * * * *